United States Patent [19]
Von Hippel et al.

[11] Patent Number: 5,961,945
[45] Date of Patent: Oct. 5, 1999

[54] METHOD OF PRODUCING CYANO COMPOUNDS BY AMMOXIDATION

[75] Inventors: Lukas M. J. Von Hippel, Alzenau; Jörg Sauer, Rodenbach; Rüdiger Schütte, Frankurt; Manfred Sauer, Rodenbach, all of Germany; Dietrich Arntz, Mobile, Ala.

[73] Assignee: Degussa Aktiengesellschaft, Frankfurt, Germany

[21] Appl. No.: 08/970,765

[22] Filed: Nov. 14, 1997

[30] Foreign Application Priority Data

Nov. 16, 1996 [DE] Germany ............................ 196 47 527

[51] Int. Cl.⁶ .......................... C01C 3/02; C07C 253/24; C07D 213/84
[52] U.S. Cl. .......................... 423/372; 423/376; 546/286; 558/308; 558/315; 558/316; 558/320
[58] Field of Search ............................ 546/286; 558/308, 558/315, 316, 320; 423/372, 376

[56] References Cited

U.S. PATENT DOCUMENTS

| | | | |
|---|---|---|---|
| 4,339,394 | 7/1982 | Grasselli et al. | 558/315 |
| 4,342,735 | 8/1982 | Tsao | 423/356 |
| 4,447,612 | 5/1984 | Beschke et al. | |
| 4,457,905 | 7/1984 | Ebner . | |
| 4,482,719 | 11/1984 | Helmut et al. | |
| 4,521,395 | 6/1985 | Kuechler . | |
| 5,158,787 | 10/1992 | Sasaki et al. | 423/376 |
| 5,160,721 | 11/1992 | Sasaki . | |
| 5,204,079 | 4/1993 | Suresh . | |
| 5,675,012 | 10/1997 | Ohi | 546/286 |

FOREIGN PATENT DOCUMENTS

| | | |
|---|---|---|
| 0 037 123 | 10/1981 | European Pat. Off. . |
| 107 638 | 5/1984 | European Pat. Off. . |
| 121 032 | 10/1984 | European Pat. Off. . |
| 311 334 | 4/1989 | European Pat. Off. . |
| 412 924 | 4/1925 | Germany . |

OTHER PUBLICATIONS

Catalysis and Catalysts; vol A 5, pp. 328–343, 1986, Ullmann's Encyclopedia of Industrial Chemistry.

Cyanno Compounds, Inorganic, vol A 8, pp. 159–164, 1987, Ullmann's Encyclopedia of Industrial Chemistry.

85:80171 CA: See Abstract.

94:105119; See Abstract.

Umemura et al., "2,6–Dicyanophenols", Chemical Abstracts, vol. 92, No. 23, Abstract No. 198128, Jun. 9, 1980.

*Primary Examiner*—Wayne Langel
*Attorney, Agent, or Firm*—Pillsbury Madison & Sutro LLP

[57] ABSTRACT

An ammoxidizable compound is reacted with an ammonium salt, especially an inorganic ammonium salt, in the presence of a source of oxygen and an ammoxidation catalyst at 100 to 700° C., preferably 200 to 700° C., in order to produce cyano compounds of the formula R—CN, in which R is H or an organic group.

10 Claims, No Drawings

METHOD OF PRODUCING CYANO COMPOUNDS BY AMMOXIDATION

CROSS REFERENCE TO RELATED APPLICATION

This application claims priority from German Application No. 19647527.9, filed on Nov. 16, 1996, the subject matter of which is hereby incorporated herein by reference.

FIELD OF THE INVENTION

The invention relates to a method for producing cyano compounds of the general formula R—CN, in which R is H or an organic group, by ammoxidation of an ammoxidizable organic compound with a source of ammonia and a source of oxygen in the presence of an ammoxidation catalyst at a temperature in a range of 100 to 700° C.

BACKGROUND OF THE INVENTION

Ammoxidation is a well-known process in which an ammoxidizable organic compound is converted into a cyano compound in the presence of an ammoxidation catalyst at elevated temperature with ammonia and oxygen. Ammoxidation achieved industrial significance e.g. for the production of acrylonitrile from propylene, benzonitrile from toluene, phthalonitrile and terephthalonitrile from ortho- and para-xylene, 3-cyanopyridine from 3-picoline as well as hydrogen cyanide from methane (Andrussoff method)—see Ullmann's Encyclopedia of Industrial Chemistry, Vol. A5, $5^{th}$ ed. (1986), pp. 328–29, 333, 343 as well as Vol. A8, $5^{th}$ ed. (1987), pp. 159–62.

Up to the present, ammoxidation has been carried out exclusively using gaseous ammonia as the source of ammonia. Numerous catalysts have proven to be suitable for ammoxidation, e.g., binary oxides based on $Bi_2O_3$—$MoO_3$, $V_2O_5$—$MoO_3$ and $V_2O_5$—$Sb_2O_5$ for the production of organic nitriles. Refer, e.g., for the production of hydrogen cyanide by the ammoxidation of methanol or formaldehyde to EP-A 0,107,638 and EP-A 0,121,032, according to which oxides of molybdenum and iron or oxides of phosphorus and an element from the series Fe, Co, Ni, Zn, B and U are used as catalysts. Numerous catalysts for the ammoxidation of e.g. propylene can be found in EP-A 0,311,334. For the ammoxidation of methylpyridines and suitable catalysts therefor, reference can be made to U.S. Pat. Nos. 4,447,612 and 4,482,719. Ammoxidation is usually carried out at a temperature between 200 and 600° C. The Andrussoff process constitutes an exception. In this process, methane is ammoxidized to hydrogen cyanide at over 1000° C. using noble-metal catalysts (Pt-Rh lattices).

It is known from experiments conducted by Nozawa et. al., Mokuzai Gakkaishi, 27 (1), 49–53 (JP) (1981) (see Chem. Abstr. 94:105119) that hydrogen cyanide is formed in the pyrolysis of wood or cellulose treated with diammonium phosphate. As the temperature increases the amount formed increases and achieves a maximum of 10 ml HCN gas/g at 900° C., corresponding to 12 mg HCN/g burned wood. In the presence of oxygen the development of HCN is only 2 to 4 ml/g at 500 to 600° C. and the development of HCN is considerably reduced at a rise in temperature to 700° C. in the presence of oxygen. Although hydrogen cyanide is formed in this pyrolysis and diammonium phosphate can be regarded as a source for ammonia, this is not an ammoxidation since no catalyst is present. In addition, the yield of hydrogen cyanide is so low that this method cannot be considered for the industrial production of hydrogen cyanide.

It is also known that ammonium salts of organic carboxylic acids can be dehydrated at elevated temperature, approximately 300° C., with the formation of corresponding nitriles. According to CS patent 160,810 (see Chem. Abstr. 85:80171) ammonium oxalate can be converted into dicyanogen and ammonium formate can be converted into hydrogen cyanide, using the device described in this document at 300° C. An ammonium salt is used in this conversion; however, this is not an ammoxidation but rather a simple dehydration.

Ammonium salts are occasionally used in the production of ammoxidation catalysts, e.g., ammonium metavanadate according to U.S. Pat. No. 4,447,612 and ammonium paramolybdate according to EP-A 0,107,638; however, the actual ammoxidation catalyst is free of ammonium salts since the production process comprises a tempering process at 500° C. and above.

SUMMARY OF THE INVENTION

The present invention has the purpose of providing a method of producing cyano compounds, especially hydrogen cyanide, saturated and unsaturated alicyclic as well as aromatic and heteroaromatic nitriles by ammoxidation in which, instead of gaseous ammonia, another source of ammonia can be used.

The problem is solved by a method of producing cyano compounds of the general formula R—CN in which R is H or an organic group by ammoxidation of an ammoxidizable organic compound with a source of ammonia and a source of oxygen in the presence of an ammoxidation catalyst at a temperature in a range of 100 to 700° C. which is characterized in that an ammonium salt is used as a source for ammonia.

Whereas in conventional ammoxidation a gaseous, ammoxidizable, organic compound of gaseous ammonia and air as the source for oxygen is reacted in the presence of the ammoxidation catalyst, in the method of the invention an ammonium salt, preferably in the form of an aqueous or organic solution, is used as the ammonia source. The solution is brought, in extremely finely distributed form, in contact with the ammoxidation catalyst; after evaporation of the solvent, the ammoxidation takes place on the catalyst surface in the presence of an ammoxidizable organic compound.

Although the ammonium salt can also be brought into contact with the ammoxidation catalyst in a finely powdered form instead of in dissolved form, the use of a solution of the ammonium salt, especially the use of an aqueous solution of the ammonium salt is preferred since this makes possible a finer distribution, better contact and a higher yield of ammoxidizable products, that is, a higher yield of cyano compounds, can be obtained. The mechanism of the ammoxidation of the invention using ammonium salts has not been investigated in detail previously. Whether and to what extent ammonia is formed from decomposition of the ammonium salt or whether the ammonium salt itself participates in the ammoxidation has thus not yet been clarified.

Inorganic as well as organic ammonium salts can be used. Inorganic ammonium salts are preferred, especially ammonium salts of sulfuric acid, sulfurous acid, phosphoric acid, pyrophosphoric acid, phosphorous acid, hydrochloric acid and carbonic acid. The applicability of ammonium salts of sulfuric acid, phosphoric acid and hydrochloric acid is particularly important for industrial applications, since such salts accumulate in many processes as a byproduct and must be removed for possible reuse. Thus, it is a particular advantage that the method of the invention provides a new way of utilizing such ammonium salts to produce high-quality cyano compounds.

The ammoxidation of the invention can be carried out in customary reactors such as those used for reactions with solid catalysts. The catalyst can be arranged e.g. in the form of a fixed bed in a fixed-bed reactor or in the form of a fluid bed in a fluid-bed reactor. An ammonium salt, especially preferably an aqueous solution thereof, a source for oxygen, usually air, as well as an ammoxidizable organic compound are supplied in gaseous form to the reactor at the same time. At least one equivalent of an ammonium salt is supplied per nitrile group from the ammoxidizable compound to be formed; an excess in a range of 5 to 100%, especially 10 to 30%, is generally customary in ammoxidation reactions. The amount of oxygen present in the reaction chamber must correspond at least to the amount determined according to the formula equation of the ammoxidation.

DETAILED DESCRIPTION OF THE INVENTION

According to a preferred embodiment the reaction takes place in a fluid-bed reactor. The catalyst forms the fluid bed, an ammonium salt is sprayed in the form of an aqueous solution onto the fluid bed and air as well as an ammoxidizable compound are passed in gaseous form through the fluid bed. The optimal concentration of the ammonium salt solution is determined by preliminary tests.

Using oxidic ammoxidation catalysts, the ammoxidation takes place at a temperature in the range of above 100 to 700° C., preferably between 200 and 700° C., and especially between 250 and 650° C. The optimum reaction temperature is determined by preliminary tests. Such a determination is very useful since the yield of cyano compound to be produced can be significantly influenced by the temperature. The optimal temperature is influenced by the type of catalyst, the reactants and the reactor type. As follows from the examples of, e.g. the ammoxidation for producing HCN from methanol and ammonium sulfate using the catalyst, the method in accordance with the examples is preferably carried out at 350 to 500° C.

Every ammoxidizable organic compound which can be converted into a cyano compound in the conventional ammoxidation method using gaseous ammonia may also be used in the method of the invention. An important prerequisite of ammoxidizable compounds is that they or their breakdown products produced under the reaction conditions have sufficient thermal stability so that they are not further decomposed or are decomposed only to a slight extent at the selected temperature of the ammoxidation. Preferred ammoxidizable compounds contain at least one group from the series methyl, vinyl, vinylidene, methylol (—$CH_2OH$) and formyl (—CHO). The ammoxidizable compounds can be alicyclic, cyclic, aromatic or heteroaromatic compounds with one or several of the previously cited groups. Preferred compounds are e.g. primary mono-, di- and polyhydric alcohols with 1 to 12 C atoms, preferably 1 to 6 C atoms, mono- and dialdehydes with 1 to 12 C atoms, preferably monoaldehydes with 1 to 6 C atoms, straight-chain and branched alkanes and alkenes with 3 to 12 C atoms, especially 3 to 6 C atoms,
mono-, di- and trialkyl aromatic substances and -heteroaromatic substances, which alkyl group contains 1 to 3 C atoms, preferably 1 C atom, and ethers or thioethers with at least one aliphatic C atom attached to the ether oxygen or thioether sulfur. The above-referenced alkylated aromatic substances are in particular benzene and naphthalene with one or several methyl groups. The alkylated heteroaromatic substances are those which contain one or several heteroatoms selected from N, O and S, comprise 5 or 6 ring members and can contain one ring or two attached rings. Examples of preferred alkylated heteroaromatic substances are methylated pyridines such as 2-, 3- and 4-picoline and 3-methylthiophene. Preferred alkylated aromatic substances are especially toluene, ortho-, meta- and para-xylene as well as 2-methyl- and 1,4-dimethylnaphthalene. Methyl-tert.-butylether is an example of an ammoxidizable ether. The ammoxidation of the invention is particularly suited for producing hydrogen cyanide using methanol or formaldehyde as the ammoxidizable compound.

The ammoxidation in accordance with the invention can be catalyzed by any known ammoxidation catalysts. The usual ammoxidation catalysts are usually oxidic catalysts with two or more metals from the main groups and subgroups of the periodic table of elements, and, in addition, noble-metal catalysts. The catalytic components can be used as such in the method or be a component of a catalyst carrier system, which carrier is selected in particular from the series of $SiO_2$, natural and synthetic silicates, $Al_2O_3$, $TiO_2$ and $ZrO_2$. Effective catalytic components are e.g. phosphates, vanadates, molybdates and tungstates of the elements Mn, Fe, Co, Ni, Cu, Zn, Sb and Bi such as binary metal oxides based on $V_2O_5$—$Sb_2O_5$, $V_2O_5$—$MoO_3$, $Bi_2O_3$—$MoO_3$, $Fe_2O_3$—$MoO_3$, $Fe_2O_3$—$WO_3$, $TiO_2$—$MoO_3$ and $ZrO_2$—$WO_3$, which can additionally contain up to 20 atom % of one or several other oxides of Zr, Te, Mo, W, V, Cr, Mn, Fe, Co, Ni, Zn, Sn, Bi and Sb. A further effective group of catalysts is oxides of the general formula $M_aPO_x$, where M is selected from the series Mn, Fe, Co, Ni, Zn and B and a is any number between 0.8 and 2 and x is the resulting number of oxygen atoms for saturating the phosphate.

The catalyst can be used in powder form; however, it is frequently more advantageous to convert the powder into briquettes molded approximately to obtain defined flow conditions in a fixed-bed reactor or to avoid the discharge of dust from a fluid-bed reactor. It is also possible to fix the catalyst on the surface of channels of a monolithic catalyst block.

The acid on which the ammonium salt is based is freed from the salt during the reaction of the invention. In as far as this freed acid is not volatile under the reaction conditions but rather precipitates on the catalyst it may be necessary to regenerate the catalyst from time to time by an appropriate washing. If ammonium sulfate is used, the sulfuric acid formed is discharged as such and/or in the form of $SO_3$ with the reaction gas from the reactor. If ammonium phosphate is used, $P_2O_5$ and/or other phosphorus oxides are produced so that a catalyst charged with such oxides must be regenerated, e.g. by washing out the catalyst with water, yielding phosphoric acid as a valuable product.

The gaseous reaction mixture leaving the reactor is worked up in a known manner. The workup generally comprises one or two washing stages in which individual components of the reaction-gas mixture can be absorbed in the washing liquid and recovered therefrom. If hydrogen cyanide is being produced using ammonium sulfate, e.g. a first washer with dilute sulfuric acid can serve for the absorption of $SO_3$ or $H_2SO_4$. The reaction gas leaving the first washer can either be conducted through a washer operated with sodium hydroxide solution, during which hydrogen cyanide is converted into sodium cyanide; or, according to an alternative embodiment, the reaction gas from the first washer is treated in a countercurrent column with cold water, during which hydrogen cyanide is absorbed and can be obtained therefrom after stabilization by rectification in liquid form. In the production of nitriles the workup comprises as a rule a wash and/or one or more distillation/rectification steps.

The invention makes it possible for the first time to use ammonium salts, which accumulate in many processes as byproducts, in ammoxidation as a source for ammonia instead of the previously customary source which was gaseous ammonia. As concerns the ammoxidation catalyst and the reaction temperature, the method closely follows previously known methods for carrying out an ammoxidation; however it differs from the latter in that the ammonium salt is brought into contact with the other reaction components and the catalyst, in the reaction chamber, in a suitable manner, preferably in the form of an aqueous solution.

The invention is further explained in the following examples.

EXAMPLES

A steel tube with a diameter of 63 mm located in an electrically heated furnace serves as an ammoxidation reactor. A 1 cm high bed of an ammoxidation catalyst produced according to Example 1 of U.S. Pat. No. 4,447,612, based on $Sb_2O_3$, $V_2O_5$, $TiO_2$, montmorillonite and $SiO_2$ (BET surface 200 $m^2/g$) was placed in this steel tube. The catalytic layer was held in the reaction tube by quartz wool. The educts, namely, a 40% by weight aqueous ammonium sulfate solution, methanol and air were supplied separately to the reactor. The ammonium sulfate solution was sprayed into the reactor from the top by means of a single-fluid nozzle in such a manner that, if possible, no drops of liquid contacted the reactor wall. Methanol was added in pre-evaporated form above the catalyst and air introduced into the top of the reactor. The reaction gas was drawn off at the lower end of the reactor. The reaction gases were first conducted through a washer with dilute sulfuric acid and then through a washer with sodium hydroxide solution. After the end of the test the cyanide content in the wash solution of the second washer was determined trimetrically.

Table 1 shows the amounts added, the reaction temperature (furnace) and the yields of HCN. It can be determined that the reaction conditions were not optimized and that between 25 and 50% of the ammonium sulfate used was separated before the catalytic bed. The yield values indicated in the table refer to reacted nitrogen components (ammonium sulfate crystallized out before the catalyst was not included in the calculation of yield). Even under the very simple and in no way optimized conditions of the tests performed it was surprisingly possible to obtain an HCN yield of above 50% relative to reacted nitrogen.

TABLE

| Example No. | 1 | 2 | 3 | 4 | 5 | 6 | 7 | 8 |
|---|---|---|---|---|---|---|---|---|
| Infeed: | | | | | | | | |
| Methanol (mmol/h) | 75 | 75 | 75 | 75 | 150 | 150 | 150 | 150 |
| $(NH_4)_2SO_4$ | 55 | 55 | 55 | 55 | 110 | 110 | 110 | 110 |
| Air (mmol $O_2$/h) | 650 | 650 | 650 | 650 | 1000 | 1000 | 1000 | 1000 |
| Furnace temp. (°C.) | 550 | 350 | 370 | 390 | 410 | 430 | 450 | 470 |

TABLE-continued

| Example No. | 1 | 2 | 3 | 4 | 5 | 6 | 7 | 8 |
|---|---|---|---|---|---|---|---|---|
| HCN yield (%) rel. to reacted nitrogen | 0.3 | 14 | 22 | 24 | 33 | 56 | 43 | 36 |

What is claimed is:

1. A method of producing cyano compounds of the general formula R—CN in which R is H or an organic group, comprising ammoxidizing an ammoxidizable organic compound by contacting said ammoxidizable organic compound with a source for ammonia and a source for oxygen in the presence of an ammoxidation catalyst at a temperature in a range of 100 to 700° C., wherein the source for ammonia is an ammonium salt.

2. The method according to claim 1, wherein the ammonium salt is a member selected from the group consisting of ammonium salts of sulfuric acid, phosphoric acid, hydrochloric acid and carbonic acid.

3. The method according to claim 1, wherein the ammoxidizable organic compound is a member selected from the group consisting of primary mono- and dialcohols with 1 to 12 C atoms, $C_1$- to $C_{12}$ mono- and dialdehydes, alkanes and alkenes with 3 to 12 C atoms, $C_1$- to $C_3$ mono- and dialkylated aromatic substances or heteroaromatic substances and ethers with at least one aliphatic C atom on the ether oxygen.

4. The method according to claim 1, comprising carrying out the reaction at 200 to 700° C.

5. The method according to claim 4 comprising carrying out the reaction at 250 to 650° C.

6. The method according to claim 1, comprising bringing the ammonium salt into contact with the ammoxidation catalyst in aqueous solution or in organic solution.

7. The method according to claim 1, comprising carrying out the reaction in a fluid-bed reactor, wherein the catalyst forms a fluid bed, an aqueous ammonium salt solution is sprayed onto the fluid bed and air and an ammoxidizable compound are passed in gaseous form through the fluid bed.

8. The method according to claim 1, wherein the ammoxidation catalyst is a member selected from the group consisting of (i) binary metal oxides based on $V_2O_5$—$Sb_2O_5$, $V_2O_5$—$MoO_3$, $Bi_2O_3$—$MoO_3$, $Fe_2O_3$—$MoO_3$, $Fe_2O_3$—$WO_3$, $TiO_2$—$MoO_3$ and $ZrO_2$—$WO_3$, which can additionally contain up to 20 atom % of one or several other oxides of Zr, Te, Mo, W, V, Cr, Mn, Fe, Co, Ni, Zn, Sn, Bi or Sb, (ii) oxides of the formula $M_aPO_x$, in which M is selected from the group consisting of Mn, Fe, Co, Ni, Zn and B and a is any number between 0.8 and 2 and x is the resulting number of oxygen atoms, and (iii) noble metals, which are used as such or on an oxidic carrier material.

9. The method according to claim 1, wherein methanol or formaldehyde is used as the ammoxidizable organic compound and cyano compound produced comprises hydrogen cyanide.

10. The method according to claim 1, wherein a methylpyridine is used as the ammoxidizable organic compound and a corresponding cyanopyridine is produced therefrom.

* * * * *